(12) United States Patent
Gazzani Romolo et al.

(10) Patent No.: US 10,675,445 B2
(45) Date of Patent: Jun. 9, 2020

(54) TRANSCRANIAL FASTENING DEVICE FOR DRAINAGE CATHETERS

(71) Applicants: GUALADISPENSING S.P.A., Alessandria (IT); GUALAPACK S.P.A., Alessandria (IT)

(72) Inventors: Igino Gazzani Romolo, Alessandria (IT); Giannantonio Spena, Alessandria (IT)

(73) Assignee: GUALADISPENSING S.P.A. (IT)

( * ) Notice: Subject to any disclaimer, the term of this patent is extended or adjusted under 35 U.S.C. 154(b) by 290 days.

(21) Appl. No.: 15/539,086

(22) PCT Filed: Jan. 7, 2016

(86) PCT No.: PCT/IT2016/000001
§ 371 (c)(1),
(2) Date: Jun. 22, 2017

(87) PCT Pub. No.: WO2016/132390
PCT Pub. Date: Aug. 25, 2016

(65) Prior Publication Data
US 2017/0361069 A1    Dec. 21, 2017

(30) Foreign Application Priority Data

Feb. 16, 2015 (IT) .............................. TO2015A0101

(51) Int. Cl.
*A61M 25/02*        (2006.01)
*A61M 25/08*        (2006.01)
(Continued)

(52) U.S. Cl.
CPC ............ *A61M 25/04* (2013.01); *A61M 25/02* (2013.01); *A61M 27/00* (2013.01);
(Continued)

(58) Field of Classification Search
CPC .... A61B 2090/103; A61M 2025/0213; A61M 2039/025; A61M 2202/0464;
(Continued)

(56) References Cited

U.S. PATENT DOCUMENTS 2,340,423 A * 2/1944 O'Shaughnessy, Jr. ..................... F16B 19/1081
411/80.2
2,693,182 A * 11/1954 Phillips ............. A61M 16/0488
128/200.26
(Continued)

FOREIGN PATENT DOCUMENTS

GB  WO2009/047491 A1  4/2009
NL      2324790 A1    5/2011

OTHER PUBLICATIONS

International Search Report and Written Opinion dated May 18, 2016.

*Primary Examiner* — Adam Marcetich
(74) *Attorney, Agent, or Firm* — Fresh IP PLC; Aubrey Y Chen

(57) ABSTRACT

A transcranial fastening device (1) for a drainage catheter (3), comprising an external body (5) being equipped with a passage (P), the passage (P) being equipped with blocking means (9) of the drainage catheter (3) adapted to allow a sliding of the drainage catheter (3) through the passage (P) along a first movement direction (M1) and to prevent a sliding of the drainage catheter (3) through the passage (P) along a second movement direction (M2).

15 Claims, 3 Drawing Sheets

(51) Int. Cl.
*A61M 25/04* (2006.01)
*A61M 39/02* (2006.01)
*A61M 27/00* (2006.01)
*A61B 90/10* (2016.01)

(52) U.S. Cl.
CPC ...... *A61M 27/006* (2013.01); *A61M 39/0247* (2013.01); *A61B 2090/103* (2016.02); *A61M 2025/028* (2013.01); *A61M 2025/0213* (2013.01); *A61M 2039/025* (2013.01); *A61M 2039/0273* (2013.01); *A61M 2039/0294* (2013.01); *A61M 2202/0464* (2013.01)

(58) Field of Classification Search
CPC ............ A61M 27/006; A61M 39/0247; A61M 25/013; B65D 2563/107; A43C 7/08
See application file for complete search history.

(56) References Cited

U.S. PATENT DOCUMENTS

| | | | | |
|---|---|---|---|---|
| 2,820,457 | A * | 1/1958 | Phillips | A61M 16/0488 128/200.26 |
| 3,683,928 | A * | 8/1972 | Kuntz | A61M 25/0111 604/171 |
| 4,809,694 | A | 3/1989 | Ferrara | |
| 5,487,572 | A * | 1/1996 | Combot-Courrau | F16L 37/0915 285/308 |
| 5,669,935 | A * | 9/1997 | Rosenman | A61B 17/0487 606/151 |
| 5,695,224 | A * | 12/1997 | Grenier | F16L 37/091 285/104 |
| 5,713,858 | A | 2/1998 | Heruth | |
| 6,126,663 | A * | 10/2000 | Hair | A61B 17/688 606/324 |
| 6,190,372 | B1 * | 2/2001 | Racz | A61M 39/0613 128/912 |
| 6,854,694 | B1 * | 2/2005 | Van Etten | A61M 5/1418 248/62 |
| 2003/0155767 | A1 * | 8/2003 | Hardie | F16L 25/0045 285/319 |
| 2005/0167994 | A1 * | 8/2005 | Debrody | G09F 3/037 292/307 R |
| 2005/0173922 | A1 * | 8/2005 | Coquard | F16L 37/0915 285/308 |
| 2009/0030443 | A1 * | 1/2009 | Buser | A61B 17/3423 606/185 |
| 2009/0088826 | A1 * | 4/2009 | Bedenbaugh | A61N 1/0539 607/116 |
| 2009/0160179 | A1 * | 6/2009 | Ericksen | F16L 37/008 285/24 |
| 2011/0140417 | A1 * | 6/2011 | Kluss | B25B 27/10 285/345 |
| 2012/0136397 | A1 * | 5/2012 | Ralph | A61B 17/688 606/300 |
| 2014/0155859 | A1 | 6/2014 | Bonde | |
| 2014/0276529 | A1 * | 9/2014 | Bodner | A61M 25/02 604/500 |
| 2015/0145248 | A1 * | 5/2015 | Hagen | F16L 37/091 285/340 |
| 2015/0252832 | A1 * | 9/2015 | Le Grange | F16B 2/08 24/582.1 |
| 2015/0352324 | A1 * | 12/2015 | Palmer | A61M 25/0111 604/544 |

* cited by examiner

TRANSCRANIAL FASTENING DEVICE FOR DRAINAGE CATHETERS

This application is a national stage entry under 35 U.S.C. 371 of international patent application PCT/IT2016/000001, and claims the benefit of Italian patent application No. TO2015A000101, filed Feb. 16, 2015, which is hereby incorporated by reference in its entirety.

FIELD OF THE INVENTION

The present invention relates to a transcranial fastening device of drainage catheters.

BACKGROUND

For the treatment of particular brain pathologies, such as, for example, subdural hematomas, ventriculitis or hydrocephalus, it is necessary to insert, through the skin and the skull, at least one drainage duct or catheter for sucking and removing blood or cerebral-spinal fluid, sending it towards a collecting tank.

Therefore, to allow making a transcranial passage and inserting this related drainage duct, it is usually necessary to proceed by neuro-surgically operating, through a perforation with a drill, the skullcap and the following coagulation and incision of the dura mater.

Examples of known techniques, processes and instruments related to such operations are disclosed, for example, in CN-A-202604860, DE-A-102005013720, CN-A-201389060, CN-A-201108493, U.S. Pat. No. 6,673,022.

In such known techniques, however, there is no device which prevents the accidental withdrawal of the drainage duct, once having implanted it, from its own transcranial passage, unfortunately requiring the execution of a new neurosurgical intervention to re-insert it, with related obvious problems on a patient.

Further, known solutions like the above described ones do not generally allow an aesthetically acceptable closure, since, not rarely, the skin tissue next to the transcranial passage tends to form valleys.

SUMMARY

Therefore, an object of some embodiments of the present invention is solving the above prior art problems by providing a transcranial fastening device for drainage catheters to prevent them from being inadvertently withdrawn.

Another object of some embodiments of the present invention is providing a transcranial fastening device which allows the closure of the transcranial passage, a healing of the skin tissue and an aesthetically better result with respect to what is offered by prior art systems.

The above and other objects and advantages, as will appear from the following description, are obtained with a device according to some embodiments of the present invention.

It is intended that all enclosed claims are an integral part of the present description.

It will be immediately obvious that numerous variations and modifications (for example related to shape, sizes, arrangements and parts with equivalent functionality) can be made to what is described, without departing from the scope of the invention as appears from the enclosed claims.

BRIEF DESCRIPTION OF THE DRAWINGS

The present invention will be better described by some preferred embodiments, provided as a non-limiting example, with reference to the enclosed drawings, in which.

DETAILED DESCRIPTION OF EMBODIMENTS

Figure 1:
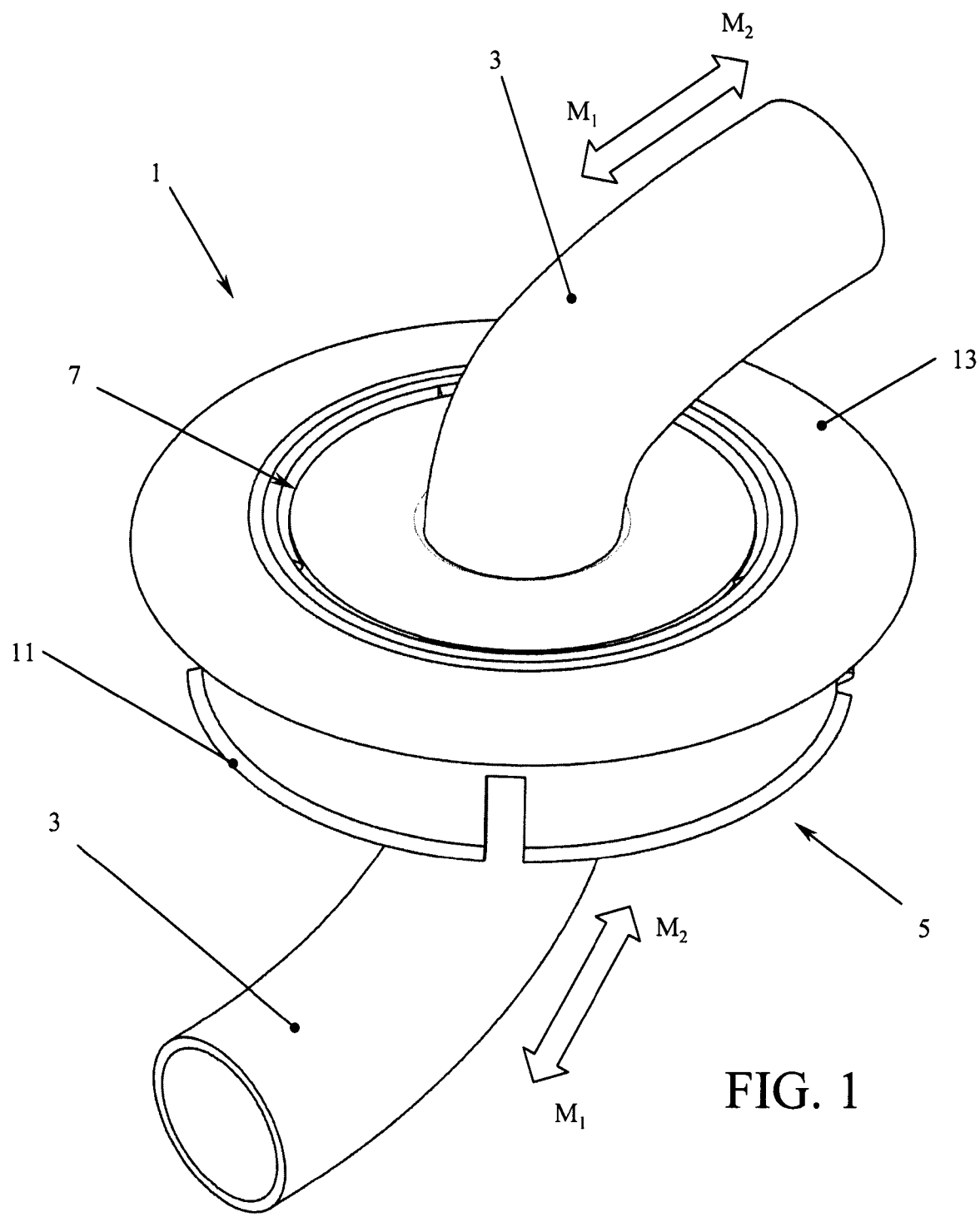
FIG. 1 shows a top perspective view of a preferred embodiment of the transcranial fastening device for drainage catheters.
Figure 2A:
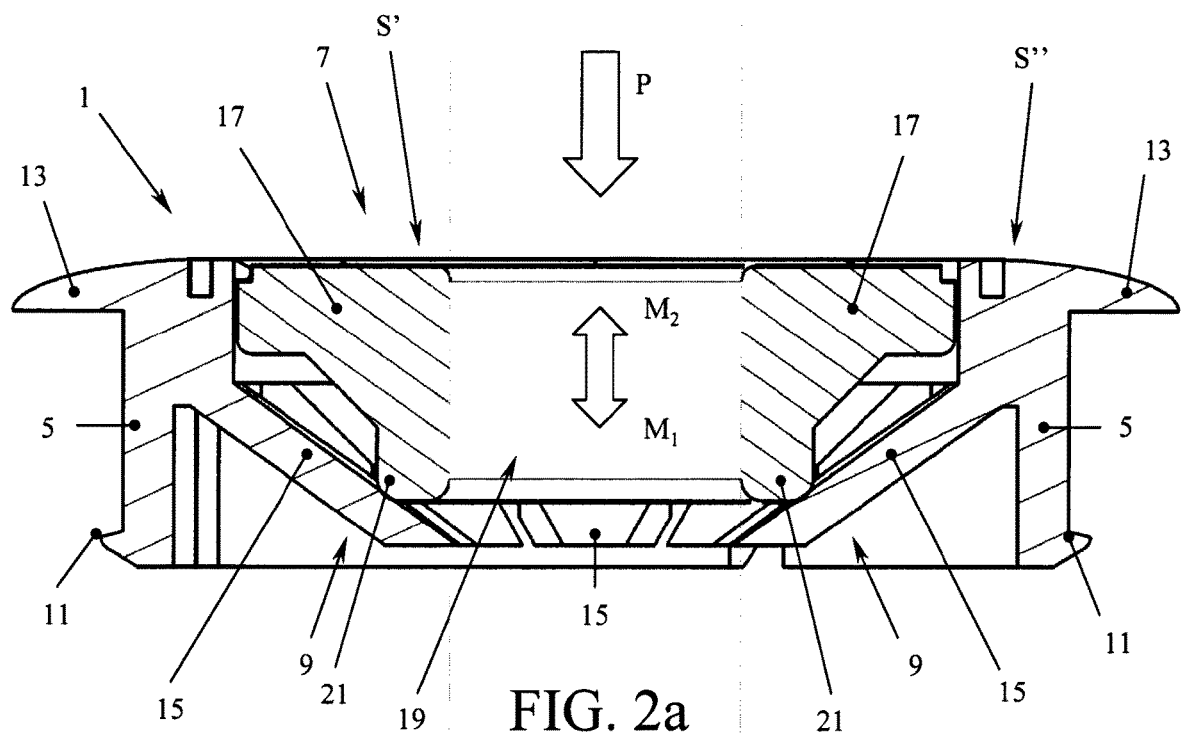
FIG. 2a shows a side sectional view of the device in a first operating position thereof.
Figure 2B:
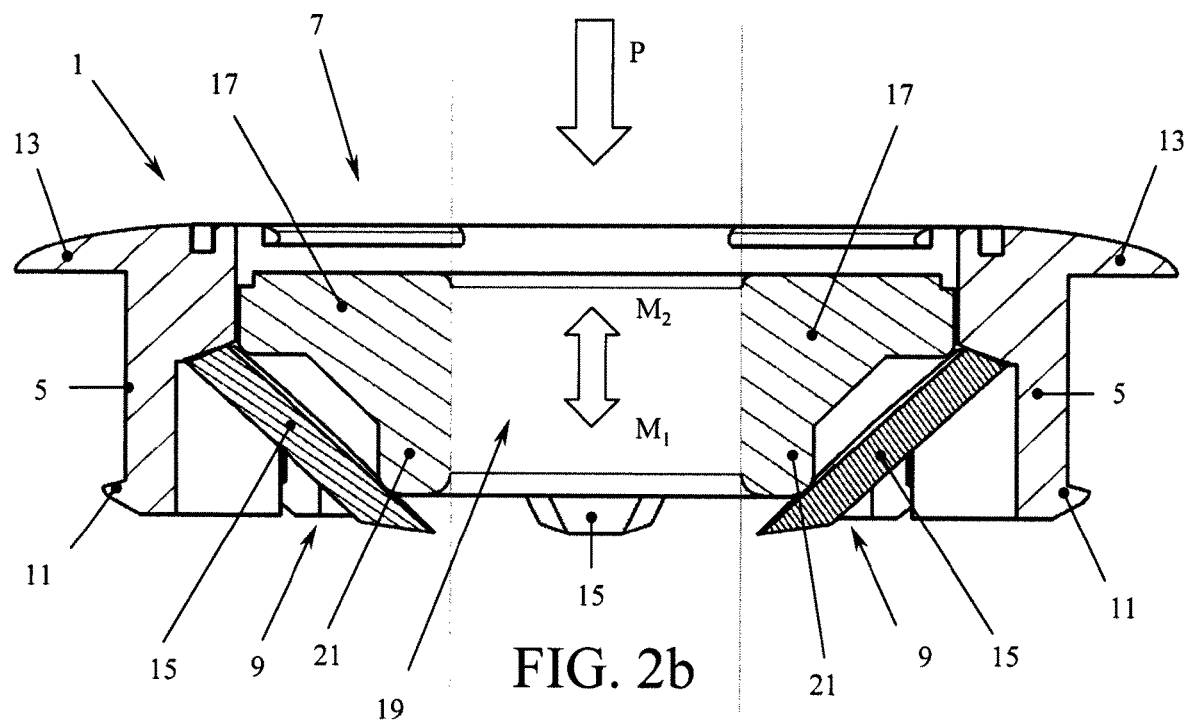
FIG. 2b shows a side sectional view of the device in a second operating position thereof.

With reference to the Figures, it is possible to note that the device 1, aimed in particular to the transcranial fastening of at least one drainage catheter 3, comprises:

at least one external body 5 adapted to be inserted inside a transcranial drilling hole, such external body 5 being equipped with at least one passage P of the drainage catheter 3 through the external body 5 itself, the passage P being equipped with blocking means 9 of the drainage catheter 3 adapted to allow the sliding of the drainage catheter 3 through the passage P along a first movement direction $M_1$ (corresponding to the insertion direction of the drainage catheter 3 from outside to inside the skull through the transcranial drilling hole) and to prevent the sliding of the drainage catheter 3 through the same passage P along a second movement direction $M_2$ (corresponding to the extraction direction of the drainage catheter 3 from inside the skull towards outside through the transcranial drilling hole);

at least one actuating means 7 operatively cooperating with the blocking means 9 and adapted to pass from a first operating position (like the one shown, for example, in FIG. 2a), which preferably corresponds with a spontaneous rest position thereof, in which the blocking means 9 do not allow the sliding of the drainage catheter 3 through the passage P of the external body 5 along the second movement direction $M_2$, to a second operating position (like the one shown, for example, in FIG. 2b) in which the blocking means 9 allow the sliding of the drainage catheter 3 through the passage P of the external body 5 along the second movement direction $M_2$.

Preferably, the external body 5 can be equipped with fastening means to the perimeter bone walls of the transcranial drilling hole in order to consolidate the connection of the device 1 with the hole itself.

Preferably, the fastening means comprise at least one undercut profile 11 arranged on the external surface of the external body 5, such undercut profile 11 being elastic enough to guarantee an adequate mechanical grip on the tissue of the perimeter bone walls of the transcranial drilling hole. Obviously, the fastening means can be made in any other way suitable for such purpose, also comprising the use of gluing substances, without thereby departing from the scope of the present invention.

Further, in order to avoid an excessive insertion of the device 1 inside the drilling hole, it can comprise at least one abutment profile 13 radially arranged around the external body 5 to abut against the external surface of the skullcap adjacent to the drilling hole itself.

The blocking means 9 comprise a plurality of unidirectional flexible wings 15 radially arranged around the passage P of the external body 5 and suitably oriented in such a way as to form a circle for the passage of the drainage catheter 3, substantially coaxial with the passage P, and offer a flexure in favor of the sliding of the drainage catheter 3 along the first movement direction $M_1$ through the passage P and the circle and, without the intervention of the actuating means 7 which can be spontaneously found in their first operating position, to be stopped dead on the external surface of the drainage catheter 3 to prevent the sliding of the drainage catheter 3 along the second movement direction $M_2$ through the passage P itself.

Advantageously, the actuating means 7 operatively cooperating with the blocking means 9 as unidirectional flexible wings 15 are therefore preferably composed of at least one cursor 17 axially sliding inside the passage P of the external body 5 along the direction $M_1$-$M_2$ and equipped with at least one through-hole 19 coaxial with the passage P to be crossed by the drainage catheter 3; the cursor 17 is further equipped with at least one abutment portion 21 cooperating with the unidirectional flexible wings 15 so that, when an external force directed along the first movement direction $M_1$ is applied on the cursor 17, this latter one passes from its first operating position (like the one shown, for example, in FIG. 2a) to its second operating position (like the one shown, for example, in FIG. 2b) in which the interaction of the abutment portion 21 against the wings 15 elastically opens these latter ones wide, with the consequent enlargement of the circle for passing defined thereby, to allow the sliding of the drainage catheter 3 through the passage P of the external body 5, and in particular through the through-hole 19 of the cursor 17, along the second movement direction $M_2$. Once the action of the external force has ceased, the elasticity of the wings 15, acting on the abutment portion 21, takes back the cursor 17 to its first operating position: advantageously, in the first operating position, which is also kept once the drainage catheter 3 is completely extracted, the external surface S' of the cursor 17 is coplanar with the external surface S" of the external body 5, and possibly with the abutment profile 13, so that the skin tissue over the device 1 does not form unaesthetic valleys.

Preferably, the external body 5 is made as an external bush in any plastic material suitable for such purpose. Moreover, the same cursor 17 can be made as an internal bush to the passage P of the external body 5 in any plastic material suitable for such purpose.

Depending on what has been described above, the device 1 is then inserted into the drilling hole, in which it is stably fastened, possibly also due to the action of the fastening means of the external body 5: afterwards, the actuating means 7 are, preferably spontaneously, in their first operating position and the blocking means 9, and in particular the unidirectional flexible wings 15, allow inserting the drainage catheter 3 through the passage P, and in particular through the through-hole 19 of the cursor 17, till its optimum positioning, but preventing its extraction, they advantageously avoid accidental withdrawals of the catheter 3 itself. Instead, once it is necessary to voluntarily remove the drainage catheter 3, it is enough to operate on the actuating means 7, for example by applying from outside the force directed along the first movement direction $M_1$, which, being taken in its second operating position, acts sui blocking means 9, for example elastically opening the wings 15 wide, to allow extracting the catheter 3 itself from the drilling hole through the passage P of the external body 5.

Figure 3:
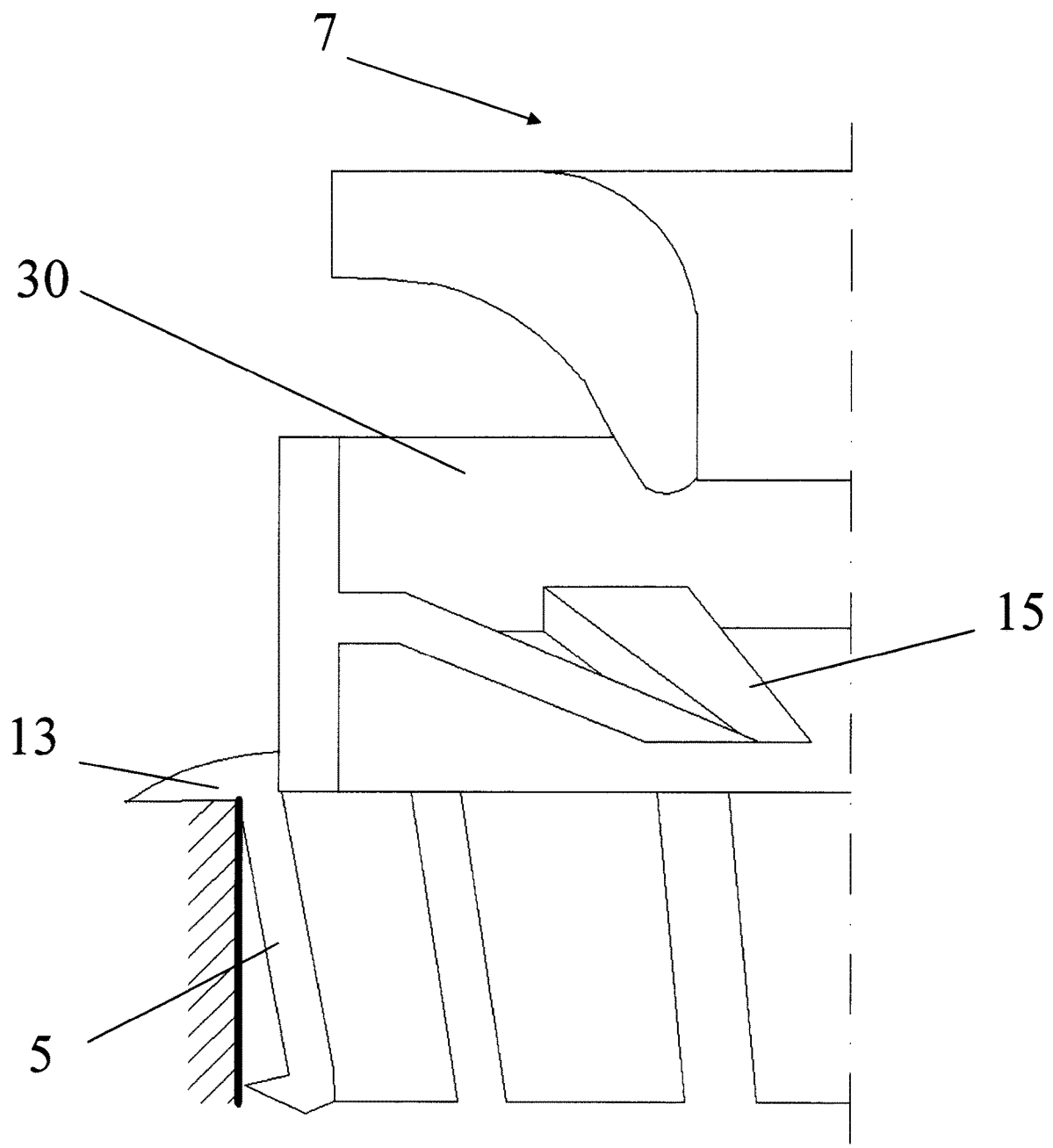
FIG. 3 shows a variation of the device.

According to the variation embodied in FIG. 3, the device 1 is made of three separate components: the external body 5 equipped with the abutment profile 13; an insert 30 equipped with the flexible blocking wings 15 adapted to be inserted with pressure inside the external body 5 in order to widen outwards the abutment profile 13 for blocking the external body 5 against the skullcap; and the actuating means 7 adapted to allow placing with a thrust the insert 30 inside the external body 5.

The invention claimed is:

1. Transcranial fastening device for at least one drainage catheter, comprising:
at least one external body adapted to be inserted inside a transcranial drilling hole, said external body being equipped with at least one passage (P) for said drainage catheter, said passage (P) being equipped with one or more blockers of said drainage catheter adapted to allow a sliding of said drainage catheter through said passage (P) along a first movement direction ($M_1$) and to prevent a sliding of said drainage catheter through said passage (P) along a second movement direction ($M_2$); and
at least one actuator operatively cooperating with said blocker, the at least one actuator being adapted to be moved from a first operating position, in which said blockers do not allow the sliding of said drainage catheter through said passage (P) along said second movement direction ($M_2$), to a second operating position, in which said blockers allow the sliding of said drainage catheter through said passage (P) along said second movement direction ($M_2$),
wherein said device comprises at least one abutment profile radially arranged around said external body and configured to abut a skullcap adjacent to said drilling hole,
wherein said blockers comprise a plurality of unidirectional flexible wings radially arranged around said passage (P) of said external body and oriented to offer a flexure in favor of the sliding of said drainage catheter along said first movement direction ($M_1$) through said passage (P) and, without the intervention of said actuator which is in said first operating position, to be stopped on an external surface of said drainage catheter to prevent the sliding of said drainage catheter along said second movement direction ($M_2$) through said passage (P), and
wherein said flexible wings and an inner wall of said passage are integrally formed.

2. Device according to claim 1, wherein said first operating position corresponds to a spontaneous rest position of said actuator.

3. Device according to claim 2, wherein said external body is equipped with one or more fasteners configured to fasten to the perimeter bone walls of said transcranial drilling hole.

4. Device according to claim 3, wherein said fasteners comprise at least one undercut profile arranged on an external surface of said external body.

5. Device according to claim 1, wherein said actuator is composed of at least one cursor axially sliding inside said passage (P) of said external body along said direction $M_1$-$M_2$ and equipped with at least one through-hole coaxial with said passage (P) to be crossed by said drainage catheter said cursor being further equipped with at least one abutment portion cooperating with said unidirectional flexible wings so that, when an external force directed along said first movement direction ($M_1$) is applied to said cursor, said cursor passes from its first operating position to its second operating position in which an interaction of said abutment portion against said wings elastically opens said wings wide to allow the sliding of said drainage catheter through said passage (P) of said external body along said second movement direction ($M_2$).

6. Device according to claim 5, wherein, once an action of said external force has ceased, an elasticity of said wings acting on said abutment portion takes back said cursor to its first operating position.

7. Device according to claim 6, wherein, in said first operating position, an external surface S' of said cursor is coplanar with an external surface (S") of said external body.

8. Device according to claim 5, wherein said external body is made as an external bush and said cursor is made as an internal bush to said passage (P) of said external body.

9. Device according to claim 1, wherein the fastening device further comprises an insert equipped with said flexible blocking wings and adapted to be inserted with pressure inside said external body in order to deform said external body outwards to expand the diameter of said external body, thereby allowing said abutment profile to block said external body against the skullcap, wherein said at least one actuator is adapted to apply a downward force to said insert while said insert is inside said external body.

10. Device according to claim 1, wherein each of said plurality of unidirectional flexible wings is arranged at an acute angle relative to said passage (P).

11. Device according to claim 1, wherein each of said plurality of unidirectional flexible wings has a first position and a second position, the first position being defined as a position of each wing after the flexure in favor of the sliding of said drainage catheter along said first movement direction ($M_1$) through said passage (P), and the second position being defined as a position of each wing after the sliding of said drainage catheter along said second movement direction ($M_2$) through said passage (P).

12. Device according to claim 1, wherein each of said plurality of unidirectional flexible wings has a distal end and a free end, and wherein said at least one abutment profile contacts each of said plurality of unidirectional flexible wings at its distal end.

13. Device according to claim 1, wherein at least one point on said at least one actuator is closer to a central axis of the passage than any point on any of said plurality of unidirectional flexible wings when said plurality of unidirectional flexible wings flexed, but not when said plurality of unidirectional flexible wings are not flexed.

14. Device according to claim 5, wherein said at least one abutment portion is in constant contact with said plurality of unidirectional flexible wings.

15. Transcranial fastening device for at least one drainage catheter, comprising:
at least one external body adapted to be inserted inside a transcranial drilling hole, said external body being equipped with at least one passage (P) for said drainage catheter, said passage (P) being equipped with one or more blockers of said drainage catheter adapted to allow a sliding of said drainage catheter through said passage (P) along a first movement direction ($M_1$) and to prevent a sliding of said drainage catheter through said passage (P) along a second movement direction ($M_2$); and
at least one actuator operatively cooperating with said blocker, the at least one actuator being adapted to be moved from a first operating position, in which said blockers do not allow the sliding of said drainage catheter through said passage (P) along said second movement direction ($M_2$), to a second operating position, in which said blockers allow the sliding of said drainage catheter through said passage (P) along said second movement direction ($M_2$),
wherein said device comprises at least one abutment profile radially arranged around said external body and configured to abut a skullcap adjacent to said drilling hole,
wherein said blockers comprise a plurality of unidirectional flexible wings radially arranged around said passage (P) of said external body and oriented to offer a flexure in favor of the sliding of said drainage catheter along said first movement direction ($M_1$) through said passage (P) and, without the intervention of said actuator which is in said first operating position, to be stopped on an external surface of said drainage catheter to prevent the sliding of said drainage catheter along said second movement direction ($M_2$) through said passage (P), and
wherein said flexible wings and an inner wall of said passage are integrally formed.

* * * * *